United States Patent [19]

Baitella

[11] 4,431,329

[45] Feb. 14, 1984

[54] ARTICULATED SUPPORT STAND

[76] Inventor: Carlo Baitella, Ohmstrasse 26/28, 8050 Zurich, Switzerland

[21] Appl. No.: 234,746

[22] Filed: Feb. 17, 1981

[30] Foreign Application Priority Data

Feb. 15, 1980 [CH] Switzerland .......................... 1255/80
Jul. 18, 1980 [CH] Switzerland .......................... 5530/80

[51] Int. Cl.³ ............................................. F16C 11/06
[52] U.S. Cl. ..................................... 403/55; 248/276
[58] Field of Search ................. 403/54, 55, 56, 90; 248/276

[56] References Cited

U.S. PATENT DOCUMENTS 3,240,516  3/1966  Barish et al. .......................... 403/54
3,910,538  10/1975 Baitella .............................. 403/56 X
4,320,884  3/1982  Leo ..................................... 248/276

FOREIGN PATENT DOCUMENTS 608874  1/1979  Switzerland ........................ 248/276

*Primary Examiner*—Andrew V. Kundrat

*Attorney, Agent, or Firm*—Scully, Scott, Murphy & Presser

[57] ABSTRACT

An articulated stand contains two relatively mutually pivotable arms at whose ends there are seated moveable joint heads. With the aid of a single clamping lever there can be concurrently locked or loosened a central joint as well as the joint heads. In order to increase the force transmitted from the articulated stand, there is provided an axial bolt or king pin which, upon clamping, presses on a ball through a curve and thereby through intermediate elements fixes a joint head in the first arm through frictional contact. A sleeve which is seated on the axial bolt exerts an effect through a curve on a ball of the second arm and transmits the resultant movement during clamping to the joint head of this arm. During clamping there are concurrently pressed together two disks of the central joint. The articulated stand is suitable, for example, for applications during surgery, as well as a retractor. It can be equipped with a prestressed spring so that the arms will not immediately tip down upon loosening of the clamping lever.

14 Claims, 15 Drawing Figures

U.S. Patent  Feb. 14, 1984  Sheet 1 of 5  4,431,329
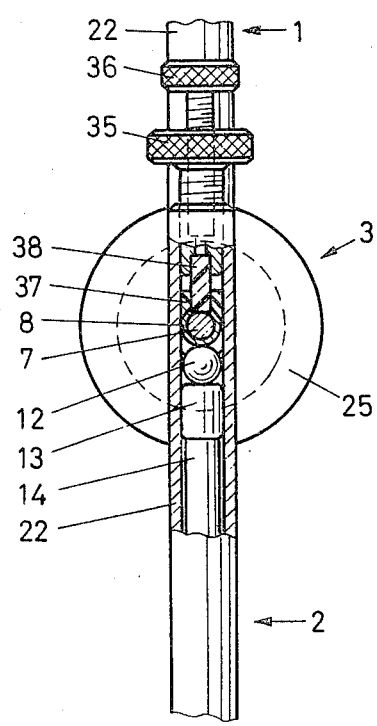
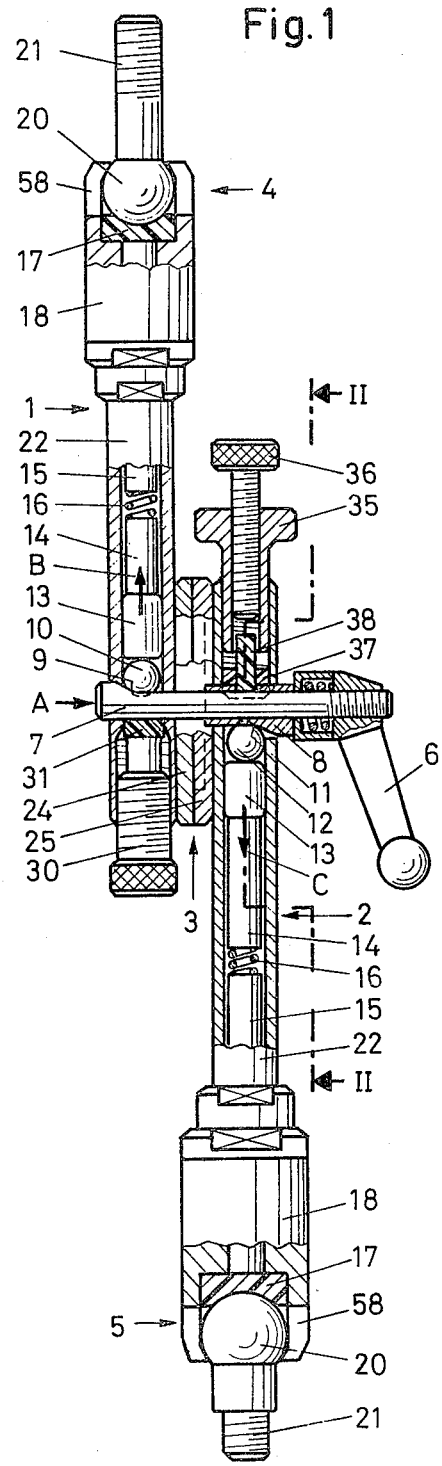

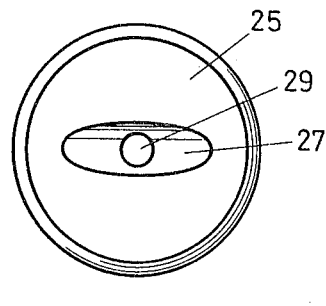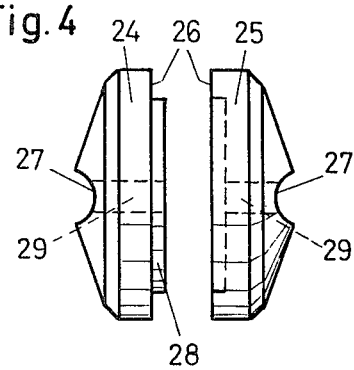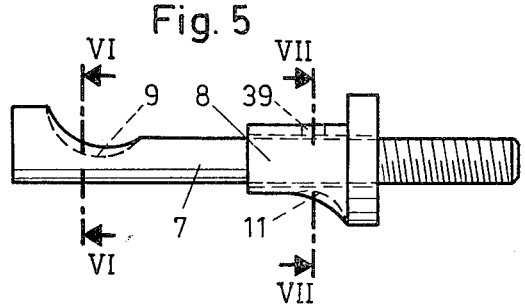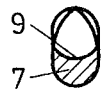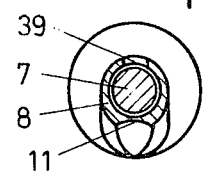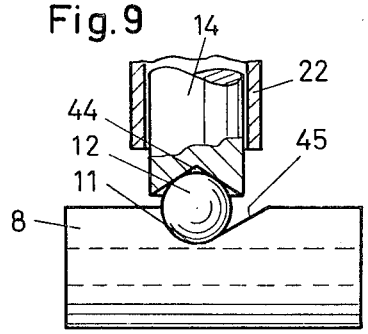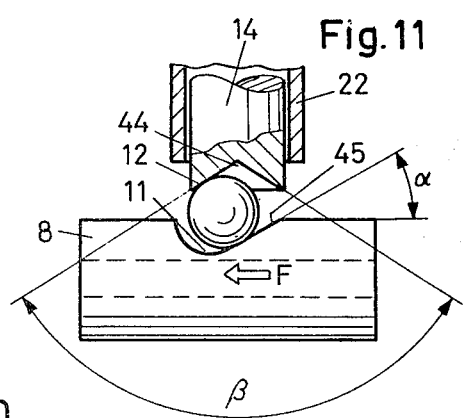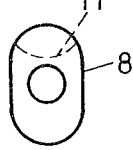

ARTICULATED SUPPORT STAND

BACKGROUND OF THE INVENTION

1. Field of the Invention

The present invention relates to an articulated support stand with at least two arms which are pivotally interconnected through the intermediary of a lockable central joint which is traversed by a king pin, and which carry ball joints at their ends, which are commonly lockable with the central joint through the utilization of a clamping member and locking members, wherein the locking elements include push rods located interiorly of the arms which act on the ball joints, and which are actuatable through an opposite relative displacement of two components provided with inclined abutting surfaces.

Articulated support stands of that type are utilized, for instance, as retractors during surgery. The articulated support stand which is equipped with the central joint and the two ball joints can be fixed in every suitable position by means of a single manipulation.

2. Discussion of the Prior Art

From U.S. Pat. No. 3,240,516 there has previously become known an articulated support stand for that type. Seated on the king pin within the central joint of this stand are two conical sleeves which act on complimentary tapered surfaces at the ends of the push rods. Upon the actuation of a clamping lever with an eccentric, the sleeves are pulled towards each other and push rods pressed outwardly. Due to the internal friction the clamping forces which are to be applied are extremely high, and the central joint must be correspondingly largely dimensioned. The wedging surface tend towards automatic locking and to seizing so they must be sufficiently lubricated which, however, renders sterilizing more difficult. The axial forces which occur during clamping have the tendency to tilt the push rods within the arm tubes.

A further articulated stand of this type of construction is described in German Published Patent Application 27 17 828. In this support stand, wedge-shaped clamping elements are forced apart through pressure rollers, whereupon the pressure is transmitted to the push rods. The central joint consists of a large number of individual components which render the manufacture more expensive and the assembling more difficult. This is particularly disadvantageous during sterilizing. In the event that the joint is not disassembled there is no protection for satisfactory sterilizing. In case that, contrastingly, it is disassembled, then the reassembly is connected with difficulties and with a large demand on time.

SUMMARY OF THE INVENTION

Accordingly, it is the primary object of the invention to avoid the above mentioned disadvantages and to so construct an articulated support stand that it can be actuated with a low demand on force, and in which the disassembly and the reassembly is also rendered problemless for unskilled personnel, which facilitates a simple, inexpensive manufacture, and which can be loaded to a higher extent than the known support stands.

The foregoing object is attained, according to the invention, in that the articulated joint as described hereinabove has the abutting surfaces arranged interiorly of two recesses, in which there are supported two balls acting on the push rod ends, in which at least one of the recesses is located in an axially displaceable sleeve on the king pin, and in which the second recess is located directly in the king pin or in a sleeve fastenable on the king pin.

Through this construction it is possible to increase the forces which can be transmitted through the articulated support stand. The individual components are better suited for mass production, and the assembly can be effected without problems after sterilizing.

A great disadvantage of the known support stands also lies in that the arms, upon loosening of the clamping member, will immediately tip down and the ball joints will yield. Thereby, work tools or instruments which are fastened to the ball joints can be destroyed upon impact. In order to avoid the foregoing, in an embodiment of the invention the central joint is equipped with a tension spring for the purpose of maintaining an adjustable arresting force at the loosening of the clamping element.

BRIEF DESCRIPTION OF THE DRAWINGS

Reference may now be had to the following detailed description of preferred embodiments of the invention, taken in conjunction with the accompanying drawings; in which:

FIG. 1 illustrates a longitudinal sectional view through a first embodiment of an articulated support stand;

FIG. 2 is a section taken along line II—II in FIG. 1;

FIG. 3 is a plan view on a disc of the central joint of the articulated stand pursuant to FIG. 1;

FIG. 4 is a side view of the two discs of the central joint;

FIG. 5 is a plan view of the king pin including the sleeve;

FIG. 6 is a section taken through the king pin along line VI—VI in FIG. 5;

FIG. 7 is a section through the king pin and the sleeve taken along line VII—VII in FIG. 5;

FIG. 9 is a schematic plan view of the sleeve seated on the king pin in an embodiment with a rollable ball, shown in the unclamped position;

FIG. 10 is a side view of the sleeve pursuant to FIG. 9;

FIG. 11 is a view similar to that of FIG. 9, however, shown in the clamped position;

DETAILED DESCRIPTION

Figure 8:
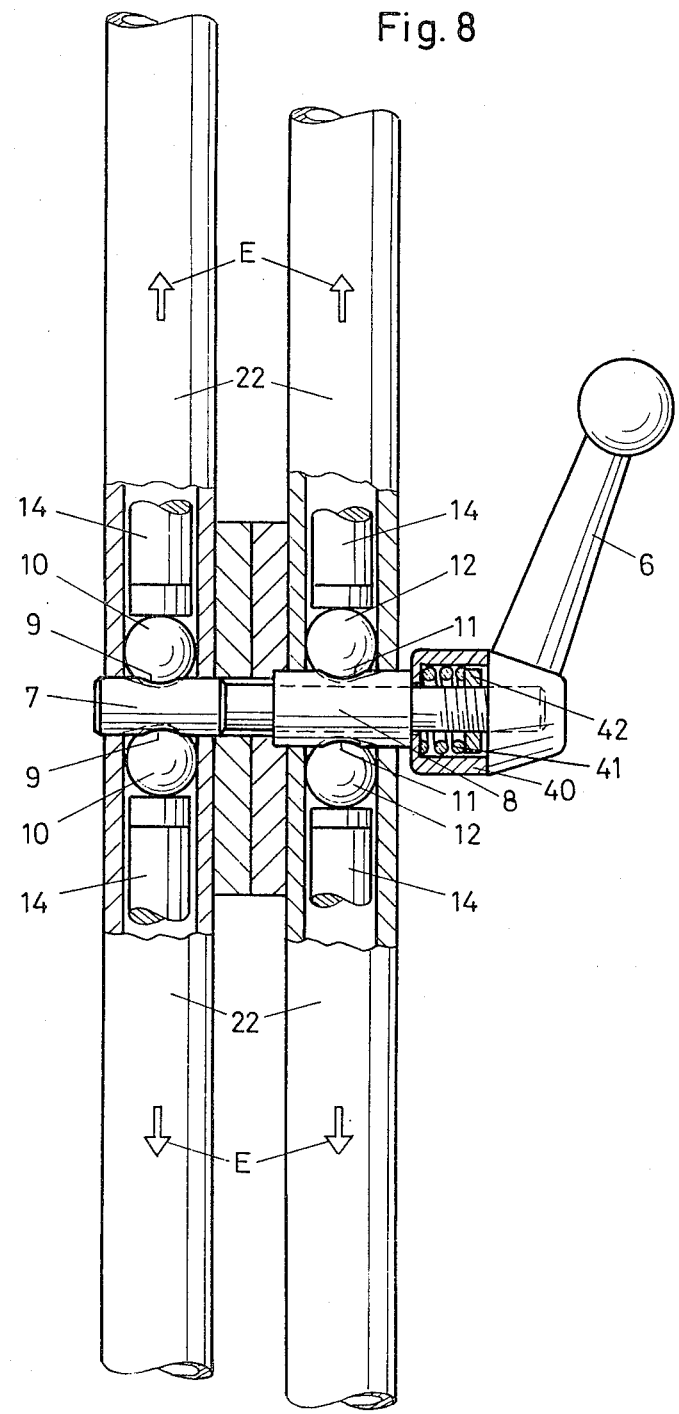
FIG. 8 is a further modified embodiment of an articulated support stand in which each arm can be provided on both sides with swivel joint heads, shown partly in section.

The articulated support stand evidences two arms 1, 2 which are pivotally interconnected through a central joint 3. Arranged at each of the ends of the arms is a movably supported swivel joint head 4, 5 with a threaded bolt 21. With the aid of a clamping element in the shape of a hand lever 6, or a hand wheel, there can be commonly locked or released the central joint 3 as well as the two swivel joint heads 4, 5. This is effected by means of a king pin or axial bolt 7 arranged to extend perpendicular to the arms, to whose end there is threaded on the hand lever 6, and which allows itself to be displaced in an axial direction relative to the arms 1, 2. A sleeve 8 is positioned over the king pin 7, and whose one end surface lies against the neighboring radial surface of the hand lever 6. The king pin 7 is provided in the region of the arm 1 with a curve-shaped recess 9. This recess 9 is arcuate in cross-section and conformed to the shape of a ball 10, as may be ascertained from FIGS. 5 and 6. A similar curve-shaped recess 11 is also located in the sleeve 8, which also operates in conjunction with a ball 12 (FIGS. 5 and 7). Located against the ball 10 is a pressure bolt 13 which is supported within the arm conduit 22, and which is in connection with a push rod inner component 14. The balls 10 and 12 are retained within the bores of the arm conduits 22 without practically any radial play, but are easily moveable. The pressure bolt 13 and the push rod inner component 14 can consist of either separate parts or of a unitary piece. A push rod external component 15 is operatively connected through a compression spring 16 with the push rod inner component 14. The component 15 is located against a ball socket 17 which is located in a ball housing 18 and which is rotatably supported about the arm axis. The ball socket 17 presses against a ball-bearing stand bolt 20 which, due to the groove 58, is pivotable about 180°. The interior of the arm 2 is constructed the same as is the arm 1, wherein the two components are provided the same reference numerals.

The central joint 3, pursuant to FIG. 4, incorporates two discs 24, 25. These have their end surfaces 26 contact against each other so that the end surfaces form the actual friction surfaces. In order to obtain a good mutual centering of these two discs 24, 25, a groove is provided in one and a corresponding annular projection 28 in the other. It would also be possible to additionally arrange a thin friction ring intermediate the two discs, for example, of hard rubber, wherein this friction ring is centered through the annular projection 28. The two discs 24, 25 are traversed in their central bore 29 by the axial bolt or king pin 7. Each of the two discs 24, 25 is provided at its outer surface with a lens-shaped recess 27 whose radius corresponds to that of the arms 1, 2. These recesses 27 serve for the loose receipt of the arm conduits 22.

The king pin 7 has a configuration at the end remote from the hand lever 6 which deviates from the circular shape, in particular an oval shape (see FIG. 6), which engages into a conformingly shaped transverse aperture in the arm conduit 22 so as to be fixed against rotation but slidably supported in this transverse aperture. Moreover, a portion of the sleeve 8 is provided with a configuration deviating from the circular shape, in particular an oval shape (see FIG. 7), which projects into a conforming transverse aperture in the associated arm conduit 22 and is supported therein so as to be secure against rotation but axially displaceable.

Inserted in the arm conduit 22 of the first arm, at the end located opposite the joint head 4, is a clamping screw 30 which operates in conjunction with a clamping jaw 31 adapted to be pressed against the king pin 7 when the clamping screw 30 is screwed in.

The second arm 2, at the end remote from the joint head 5, is provided with a first clamping screw 35 acting on the clamping sleeve 8 and a second clamping screw 36 acting on the king pin 7. The clamping screw 35 operates in conjunction with a clamping jaw 37 which presses against the shell of the clamping sleeve 8, when the clamping screw 35 is screwed into the arm conduit 22. The clamping screw 36 traverses a central bore in the clamping screw 35 and, through an opening 39 in the clamping sleeve 8, presses with a clamping jaw 38 against the king pin 7 when the clamping screw 36 is screwed in.

The described articulated stand functions as follows.

Through rotation of the hand lever 6 there can be concurrently obtained a locking of the two joint heads 4 and 5 in their presently assumed position, as well as a locking of the central joint 3. During the clamping sequence, in effect, during the screwing in of the hand lever 6 onto the thread of the king pin 7, the last-mentioned is drawn in the direction of the arrow A. Thereby, the ball 10 is pressed outwardly in the direction of the arrow B along the inclined, curve-shaped recess 9, whereby this movement is transmitted through the push rods 14 and 15 to the ball joint 17 and presses the latter against the ball-bearing stand bolt 20 so as to lock this in its position through frictional contact. The hand lever 6 concurrently also presses against the end surface of the clamping sleeve 8 and moves this opposite to the direction A, so that the ball 12 in the arm conduit 22 is moved in the direction of the arrow C since it abuts in the inclined, curve-shaped recess 11. This movement is once again transmitted through the push rods 14, 15 contained within the arm 2 to the ball joint 17 and thus blocks the ball-bearing stand bolt 20 of this arm 2 or, in effect, its ball joint.

As a result of the clamping movement of the hand lever 6 the two disks 24, 25 of the central joint 3 are also pressed against each other so that their end surfaces 26 are secured against rotation through frictional contact. Thus, all three joints are concurrently locked by a single hand lever 6. Also for the loosening of all three joints, the single hand lever 6 merely needs to be rotated in the opposite direction.

There is also selectively available the capability of loosening the joint of only one arm, while the ball-bearing stand bolt will retain the other arm in its locked position. In the event that this ball-bearing stand bolt 20 of the arm 1 should remain blocked, this can be undertaken through the screwing in of the clamping screw 30. This clamping screw 30 then presses with its brake jaws 31 against the king pin 7 and prevents the latter from moving axially relative to the arm 1. Thereby, the clamping force will be maintained and the ball-bearing stand bolt 20 of the arm 1 cannot be moved, whereas the two other joints are loosened.

When the clamping screw 36 is threaded in, by means of its clamping jaw 38 it will press against the axial bolt or king pin 7 and prevents the latter from being displaced in an axial direction. This effects a blocking of the position of the two disks 24, 25 the central joint 3. On the other hand, the drawing fast of the clamping screw 35 facilitates a pressing of the clamping jaw 37 against the clamping sleeve 8 so that this cannot move in the axial direction and, as a result, the ball 12 will maintain its clamped position, and as a consequence thereof the ball-bearing stand bolt 20 of the arm 2 is fixed in its position.

Illustrated in FIG. 8 is a modified embodiment in which a joint head is located at, respectively, both arm ends, which is adapted to be fixed and loosened through a clamping lever 6. The same elements are designated with the same reference numeral as in the embodiment pursuant to FIGS. 1 through 7. The difference is in the construction of the axial bolt or king pin 7 which evidences an additional curve-shaped recess 9 on the diametrically opposite side from the curve-shaped recess 9, which cooperates with a ball 10. Also the clamping sleeve 8 contains, in addition to the curve-shaped recess 11, a further diametrically oppositely located curve-shaped recess 11, against which there contacts a ball 12. The balls act in the same manner as previously described, on the push rods 14 which, at a movement in the direction of the arrows E, will fix in position the ball-bearing stand bolts 21 which are to be mounted at the arm ends; not shown in FIG. 8.

In lieu of groove-shaped recesses, the king pin 7 and the clamping sleeve 8 can each also be provided with a circumferentially encompassing curve-shaped formation in cross-section. The securing of the king pin in 7 against rotation relative to the arm conduit 22 can be achieved, in lieu of a shape pursuant to FIG. 6, also through a hexagon or other shape deviating from the circular form, or through a wedge.

In order to avoid an uncontrolled movement of these arms at a loading weight on the arms upon the loosening of the clamping lever 6, a tension spring 41 is arranged intermediate the clamping lever 6 and the end surface of the sleeve 8. This spring is located within a spring housing 40 which is connected fixed against rotation with the king pin 7 or the sleeve 8. With the aid of a disk-shaped threaded nut 42 which is introduceable into the housing, there can be adjusted the tensile force of the spring 41. Achieved hereby is that the curve-shaped recesses 9, 11 will also press at an unloaded hand lever 6 with a predetermined force against the balls 10, 12, and thereby through the push rods against the brake wedges 17 of the joint heads so that the ball-bearing stand bolts 21 will allow themselves to be brought into a new position only after overcoming a predetermined force. Also the two disks 24, 25 lie in friction contact with a compressive force against each other.

As a modified embodiment it would also be possible that, in lieu of balls 10, 12, there be utilized a cylindrical roller and rectangular conduits, or that the push rod ends be directly spherically shaped. The curves 9, 11 can also be formed in the shape of linear inclines whereby these inclines are sloped relative to the longitudinal axis of the axial bolt 7.

In the modified embodiment pursuant to FIGS. 9 through 11, the sleeve 8 is also provided with one or with two diametrically oppositely located curve-shaped recesses 11. The pressure bolt 13 or the push rod is positioned against the balls 10 or 12. In contrast with the embodiments pursuant to FIGS. 1 through 8, the ball 12 or 10 has herein a smaller diameter than the bore of the arm conduit 22. The end surface of pressure bolt 13 facing towards the ball 12 or the push rod end has a conically-shaped configuration 44 which can be constructed as a recess or as a point. The sector angle $\beta$ of this conically-shaped recess construction 44 is so selected in conformance with the wedge surface 45, that the ball 12 contacts an approximately diametrically oppositely located points on the conical surface or the curve surface. When the taper angle $\alpha$ of the wedge surface 45 is selected, for example, as 35°, then the sector angle $\beta$ of the cone 44 consists of 110°. Thereby, at a displacement of the sleeve 8 in the direction of the arrow there is obtained a pure rolling movement of the ball 12. This reduces the friction and permits for the application of a larger clamping force or retaining force at the arm ends. The conical enveloping line along which the ball 12 rolls down on the pressure bolt 13, and the line on the wedge surface 45 on which the ball 12 also rolls down, thus extend parallel or should be selected so as to extend at least approximately parallel. A steeply conically shaped configuration has the advantage that it imparts a central guidance to the ball. An analogous construction can also be selected for the curves 9 of the king pin or axial bolt 7 so that, for example, for a double-sided arranged arms pursuant to FIG. 8, all four curves and balls are correspondingly constructed.

Figure 12:
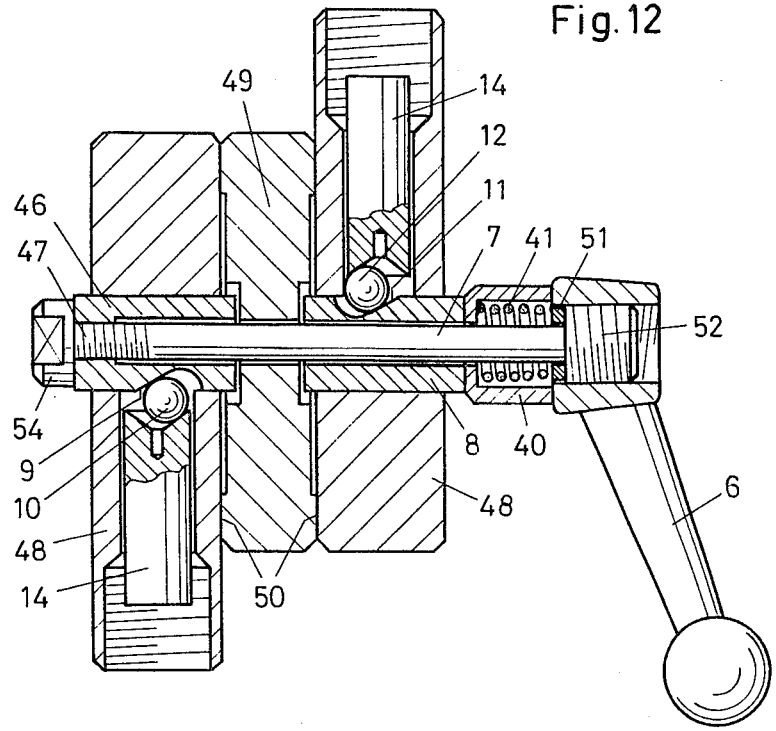
FIG. 12 is a partly sectioned side view of the central joint pursuant to a further modified embodiment.
Figure 13:
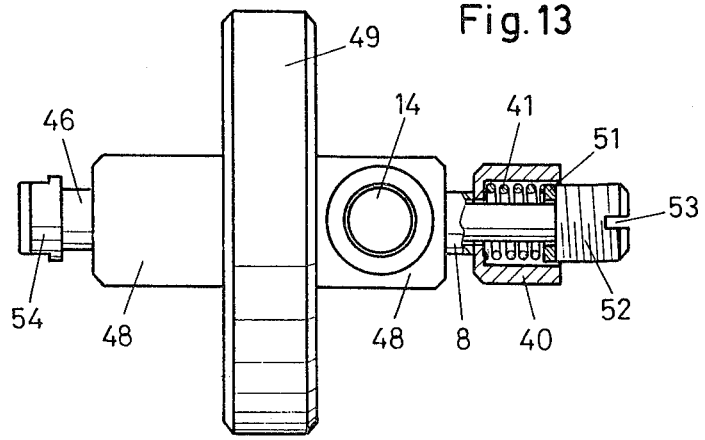
FIG. 13 is a plan view of the central joint pursuant to FIG. 12.

In the embodiment pursuant to FIGS. 12 and 13, the recess 9 is not provided directly in the axial bolt 7 but is arranged in a further sleeve 46. This sleeve is screwed onto a thread 47 at the end of the axial bolt 7 located remotely from the hand lever 6. Both sleeves 8, 46 are ovally-shaped and traverse respective cross-bores formed in the ends of the arms 1, 2. The last-mentioned are hereby fixedly seated secured against rotation on the sleeves 8, 46, however, are displaceable on these sleeves in the axial direction.

The arm ends are provided with rectangular sections 48, which cooperate with a freely rotatable friction disk 49 centrally located on the king pin 7, whereby the friction disk evidences a projecting annular surface on both sides which are determined as the actual friction surfaces. The external arm extension with the push rods and the joint heads are not illustrated in FIGS. 12 and 13.

In the event that the clamping force of the joint heads is to be varied, then the two sleeves 8, 46 and the corresponding push rod inner component 14 can be easily exchanged. Thus, for example, the arm which is fastened to a foot of the stand can cooperate with a sleeve which evidences a recess with a steeper abutting surface in comparison with the recess in the second sleeve which, for example, is determined for a work tool-supporting arm. At the clamping of the hand lever the stand-supporting arm is more intensely locked than the work tool-supporting arm. Through a corresponding selection of the shape and the slope of the abutting surfaces there can thus be influenced the clamping force and the clamping path.

Also the articulated stand pursuant to FIGS. 12 and 13 is provided with a tension spring 41 which is arranged within a spring housing 40 and is pressed against a disk 41 which, in turn, contacts against the inner end of the thread 52 for the hand lever. The spring housing 40 is supported against the end surface of the sleeve 8 which is supported so as to be freely displaceable on the axial bolt 7.

For the tensioning of the spring 41, the hand lever 6 is removed, and the axial bolt (whose end towards the hand lever is provided with a slot 53) is threaded further into the second sleeve 46. Then the locking nut 54 is tightened so that the set prestressing cannot be varied.

In contrast with the embodiment pursuant to FIGS. 1 and 8, the hand lever 6 does not directly press against the spring 41 and therefore, during clamping, need not additionally overcome the spring force. The hand lever acts through the spring housing directly on the sleeve 8 so that during clamping there is required a lower amount of force. This again effects, together with the practically negligible friction, that the articulated stand can be loaded higher than the known articulated stands.

Figure 14:
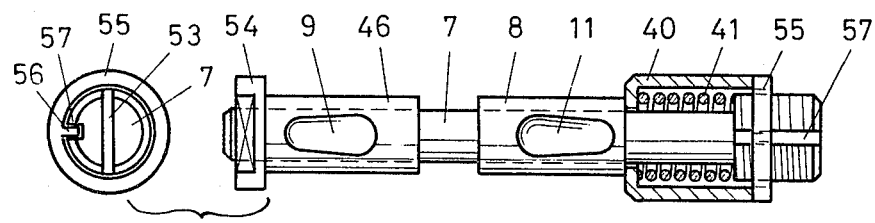
FIGS. 14 and 15 each illustrate schematically the fixed setting of the clamping for a loose and for a clamped hand lever.
Figure 15:
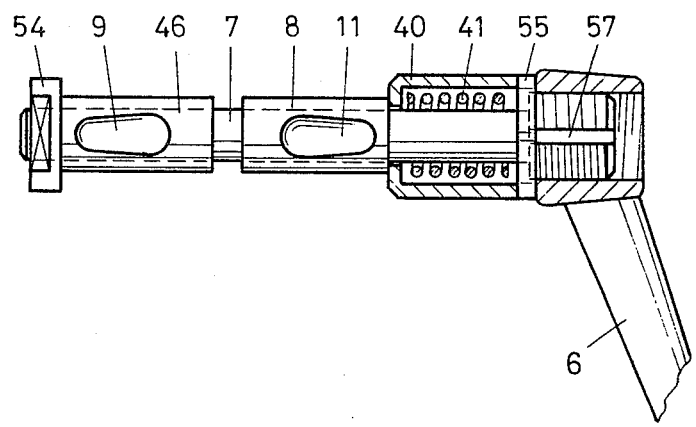

In FIGS. 14 and 15 these interrelationships are schematically illustrated. FIG. 14 illustrates the fixed setting of the prestressing with a loose or removed hand lever 6. In FIG. 14 the hand lever 6 is clamped and the spring 41 is partially unloaded.

Suitably, a base disk 55 with a projecting nose portion 56 is arranged intermediate the spring housing 40 and the clamping lever 6. The nose portion 56 penetrates into an elongated groove 57 in the axial bolt 7 so that the base disk 55 is supported as to be fixed against rotation but axially displaceable on the axial bolt 7. Thereby the clamping lever 6 can be suitably frequently loosened and clamped without its rotational movement effecting a variation in the prestressing. Also a opposite pivoting of the arm will not exert an effect on the prestressing.

The disassembly and the reassembly can be effected without problems through only a few manipulations so that even unskilled personnel can easily sterilize the articulated stand.

In order to prevent the seizing of the operatively important components in every instance, emergency running properties can be produced through surface treatment (for example, "Tenifer" treatment).

In addition to its use during operations, the present articulated stand can also be utilized for the retaining of time clocks and work tools in industry, in the laboratory and soforth.

In a further embodiment, in lieu of the adjusting nut 54 (FIGS. 12 and 13) there can be employed a knurled nut so as to provide for a stepless adjustment. The axle 46 is then not threaded together with the axial bolt 7. In lieu thereof, the sleeve 46 and the king pin or axial bolt 7 can be connected with an elongate wedge which will also secure them against rotation.

What is claimed is:
1. An articulated support stand having two arms, a fixable central joint pivotally interconnecting the arms, ball joints at the end of the arms, and means for concurrently locking the central joint and the ball joints, said stand comprising;
   (a) first and second support arms, each of said arms having a ball joint at first ends thereof, said ball joints being locked by first and second reciprocal push rods mounted for reciprocation in said first and second support arms,
   (b) a central joint for securing the second ends of said first and second support arms in a pivotal relationship, said central joint defining a pivot axis between said arms for pivotally positioning said first and second arms, said joint also including first and second friction members for restraining movement about said pivot axis when said friction members are clamped together,
   (c) an axial bolt traversing said joint and aligned with said pivot axis, said axial bolt defining a first groove being a spherical ramp cross-section aligned with the reciprocal axis of the push rod mounted in said first support arm,
   (d) a sleeve mounted for reciprocation on said axial bolt, said sleeve defining a second groove having a spherical ramp cross-section aligned with the reciprocal axis of the push rod mounted in said second support arm,
   (e) first and second balls connecting said first and second push rods with said first and second spherical grooves, wherein reciprocal movement between said bolt and said sleeve will displace the balls outwardly from said pivotal axis along the spherical ramps,
   (f) clamp means for reciprocating said sleeve along the axial bolt to simultaneously exert a clamping force on said first and second friction members and a reciprocating force on said first and second push rods to lock said ball joints.

2. A stand as claimed in claim 1, comprising a clamping screw with a clamping jaw in at least one arm acting on the axial bolt, and through which there is lockable the relative position of the axial bolt with respect to the arm.

3. A stand as claimed in claim 1, comprising a clamping screw with a clamping jaw acting on the reciprocating sleeve, said screw mounted in said second arm, and through which there is lockable the relative position of the clamping sleeve with respect to said second arm.

4. A stand as claimed in claim 1, wherein said push rods are formed of two parts with a compression spring located between the two parts.

5. A stand as claimed in claim 1, said central joint comprising two friction discs traversed by said axial bolt, each disc having a groove on the outer surface thereof for loose contact with the first and second arms.

6. A stand as claimed in claim 1, comprising an adjustable prestressing element and a tension spring in said central joint for maintaining an adjustable residual locking force at the loosening of the clamping means.

7. A stand as claimed in claim 6, said tension spring being located between said reciprocal sleeve and said clamping means.

8. A stand as claimed in claim 6, wherein one end of the tension spring remote from said reciprocal sleeve is supported against an axially fixed stop means.

9. A stand as claimed in claim 6, which further comprises a housing for supporting said tension spring therein; and a threaded nut being threaded into said housing for setting the adjustable spring prestressing.

10. A stand as claimed in claim 7, wherein the end of the axial bolt remote from the clamping element is threaded into a fixable sleeve so as to determine the spring prestressing through its threaded-in lenth.

11. A stand as claimed in claim 10, comprising a lock nut seated on the end of the axial bolt supporting the fixable sleeve.

12. A stand as claimed in claim 1, wherein the ramp surfaces constructed as spherical grooves have differing ramp slopes.

13. A stand as claimed in claim 6, which further comprises a base disc adjacent a clamping lever which is supported on said axial bolt and secured against rotation, but axially displaceable.

14. A stand as claimed in claim 13, said base disc including a nose wedge portion engaging an elongate groove in said axial bolt.

* * * * *